United States Patent [19]

Schneider

[11] 4,374,830

[45] Feb. 22, 1983

[54] PLATELET AGGREGATING MATERIAL FROM EQUINE ARTERIAL TISSUE

[75] Inventor: Morris D. Schneider, Knoxville, Tenn.

[73] Assignee: Research Corp., New York, N.Y.

[21] Appl. No.: 292,201

[22] Filed: Aug. 12, 1981

Related U.S. Application Data

[63] Continuation-in-part of Ser. No. 81,974, Oct. 4, 1979, abandoned, which is a continuation of Ser. No. 875,730, Feb. 7, 1978, abandoned.

[51] Int. Cl.³ .................... A61K 37/02; A61K 37/12; C12P 21/06; C12N 9/00; C07G 7/00
[52] U.S. Cl. ............................... 424/177; 260/112 R; 260/112.5 R; 260/117; 260/118; 424/9; 424/95; 424/101; 435/4; 435/212; 435/214; 435/268; 435/273
[58] Field of Search .............. 424/9, 95, 101, 177; 260/112.5 R, 112 R, 117, 118; 435/4, 212, 214, 268, 273

[56] References Cited

U.S. PATENT DOCUMENTS 4,347,243  8/1982  Schneider ........................ 424/177

Primary Examiner—Anna P. Fagelson
Attorney, Agent, or Firm—Wyatt, Gerber, Shoup, Scobey & Badie

[57] ABSTRACT

Novel hemostatic agent comprises equine arterial fibrillar collagen in a carrier. The agent is useful for the aggregation of platelets for clinical diagnostic tests and for the clotting of blood, such as for controlling bleeding in warm blooded species. The fibrillar collagen is obtained by extracting homogenized equine arterial tissue with aqueous solutions followed by extensive dialysis.

27 Claims, No Drawings

PLATELET AGGREGATING MATERIAL FROM EQUINE ARTERIAL TISSUE

This invention was made in the course of, or under a contract with the United States Department of Energy.

RELATED APPLICATIONS

This application is a continuation-in-part of copending application Ser. No. 81,974, filed Oct. 4, 1979, now abandoned, which in turn is a continuation application of application Ser. No. 875,730, filed Feb. 7, 1978 and now abandoned.

BACKGROUND OF THE INVENTION

Platelet aggregation is of primary importance in the clotting mechanism of blood. Materials that stimulate platelet action also promote blood clotting and are called hemostatic agents. In the prior art, it has been suspected that certain components of the arterial wall are related to platelet action. The function of the particular components, either singly or in combination, has not been well understood. The study of platelet aggregation is useful for determining the role of platelets in a variety of hemostatic diseases, and in diagnostic tests for detecting the presence of diseases characterized by abnormal platelet function or activity. A potent, highly sensitive platelet aggregating agent has long been needed.

It is an object of this invention to provide a hemostatic agent which is highly effective for promoting platelet aggregation and blood clotting.

It is a further object to provide an agent useful for studying platelet function and detecting functional disorders in the platelet aggregating mechanism.

It is a further object to provide a method for producing a highly potent hemostatic agent from arterial tissue of equine species.

It is a further object to provide a method for clotting blood and for controlling bleeding from a wound or incision.

It is a further object of this invention to provide a vasoconstrictive agent.

SUMMARY OF THE INVENTION

These and other objects have been achieved by providing a platelet aggregating hemostatic composition from equine arterial tissue. It has been discovered that the compositions of this invention will stimulate platelet aggregation when an effective amount contacts a platelet containing suspension such as platelet rich plasma or whole blood either in vitro or in vivo. A composition therefore is useful in a method for controlling external bleeding from a wound or incision by contacting the wound or incision with an effective amount of the composition either alone or with a suitable carrier. The invention also comprises a method of detecting abnormal platelet function comprising contacting a solution containing platelets suspected of abnormal function, such as plasma or whole blood, with a composition of the invention and comparing the aggregation response of the plasma or whole blood under study to the response of normal platelets.

The objects of this invention are achieved therefore according to a method for preparing hemostatic compositions comprising the steps of (a) contacting homogenized equine arterial tissue with an aqueous solution to provide an aqueous mixture containing extracted collagen species and unextracted arterial tissue; and (b) separating unextracted arterial tissue from said aqueous mixture to provide a supernatant extract containing arterial fibrillar collagen, said extract being capable of stimulating the aggregation of platelets. In its compositional aspects this invention comprises hemostatic compositions comprising a suspension of equine arterial fibrillar collagen in a carrier. In its method of use aspects, this invention comprises a method of stimulating platelet aggregation comprising contacting a platelet containing suspension such as platelet rich plasma or whole blood with an equine arterial fibrillar collagen composition. The aggregation of platelets according to this method is useful in a method for controlling bleeding from a wound or incision comprising contacting the wound or the incision with a novel composition of the invention. In its diagnostic aspects, this invention comprises a method of detecting abnormal platelet function comprising contacting a solution containing platelets such as plasma or whole blood with a composition of the invention and comparing the aggregation response of said platelets to the response of normal platelets.

DETAILED DESCRIPTION

An aspect of this invention is the discovery that equine arterial tissue contains material which can be extracted with a balanced salt solution and is highly potent for stimulating the aggregarion of platelets of warm blooded animals, including humans. Equine arteries contain lining endothelium, elastin (non-collagenous), basement membrane (amorphous collagen), and smooth muscle cells, believed to be the site of synthesis of fibrillar arterial collagen. The hemostatic compositions of this invention are extractable from homogenized arterial tissue by aqueous solutions. The aqueous extract obtained from equine arterial tissue is several times as potent as similarly obtained extracts from swine or bovine species. Additionally, it has been found that the extracted equine collagenous material is even more effective for stimulating the aggregation of human platelets than the platelets of other animals, including a homologous species.

In the first step of this invention, segments of equine arterial tissue (horse, donkey, mule, etc.) are cleaned of all loose connective tissue, adventitial layer, blood cellular fragments, platelets, plasma, etc. by extensive rinsing, is contacted with a balanced salt solution. The preferred arterial tissue is tissue from the upper thoracic aorta of the animal, extending to the diaphragm and including the common bronciocephalic trunk. The platelet aggregating material isolated in accordance with this invention is most concentrated in this portion of the arterial system. The active material appears to be present in higher amounts in older animals. Animals with overt disease symptoms or with arthero- or arterosclerosis lesions should not be used as sources of the hemostatic composition.

In the presently preferred procedure for preparing the arterial tissue to undergo the isolation procedure of this invention, the tissue is cut into small segments (approximately 5×5 mm) and thoroughly cleansed by washing or rinsing with an appropriate wash liquid. Any of a variety of physiological safe liquids including water, but preferably balanced salt solutions can be used for cleansing. Physiological saline is useful. Tyrode's solution which is a balanced salt solution simulating the salt content of mammalian body fluids and including glucose, sodium bicarbonate and magnesium salts stabilized at a pH of about 7.4 is preferred. Other balanced salt solutions such as Hank's or Earle's can also be employed.

The cleansed segments may be utilized immediately, but will normally be prespared in relatively large amounts and stored at −20° C. to −85° C. until ready for use.

The first step of the isolation procedure is to homogenize and extract the segments at low temperature, i.e. about 0° C. to 5° C. in the selected aqueous solution. The suspension is collected, and may be again homogenized and extracted. The procedure may be repeated up to eight or more times to insure complete extraction. The insoluble segments are separated to leave the extract as a useful composition of this invention.

The unextracted arterial tissue is readily separable by filtration. However, the preferred separation method is moderate centrifugation, i.e. 650 g for ten minutes. Additional centrifugation of the hemogenate tends to increase loss of suspended material to the pellet. Upon centrifugation, the unextracted material concentrates in the pellet. The supernatant extract, containing extracted material contains the hemostatic composition of this invention, and is capable of stimulating platelet aggregation. The composition can, and preferably is further concentrated and purified by a series of alternate dialyses and centrifugations.

The hemostatic compositions of this invention prepared as described in detail hereinafter contains a hemostatic agent capable of enhancing the rate of platelet aggregation in mammalian blood which is stable for extended periods of time at temperatures as low as −85° C. It loses its platelet aggregating activity when exposed to collagenase or when heated at 100° C. for fifteen minutes. It is stable at 56° C. for up to sixty minutes or when exposed to α-chymotrypsin. With repeated spearation, extraction and dialysis, it is possible to isolate from different starting materials, products which all manifest the foregoing properties and which, while not always absolutely identical, can be recognized by these properties and by the fact that they contain the following average number of amino acid residues per 1000 total amino acid residues:

| Lysine | 29.8 | Glycine | 206.5 |
|---|---|---|---|
| Histidine | 31.2 | Alanine | 133.9 |
| Hydroxylysine | 4.8 | ½ Cysteine | 13.2 |
| Arginine | 43.2 | Valine | 57.6 |
| Hydroxyproline | 20.1 | Methionine | 14.2 |
| Aspartic Acid | 65.4 | Isoleucine | 26.7 |
| Threonine | 38.1 | Leucine | 52.5 |
| Serine | 40.3 | Tyrosine | 15.3 |
| Glutamic Acid | 81.9 | Phenylalanine | 27.1 |
| Proline | 98.2 | | |

The foregoing is consistent with the fact that as with many products isolated from natural sources, particularly animal sources, the exact analysis and properties of each isolated product will vary. The composition of this invention, is however, readily identified by its platelet aggregating activity, its hypertensive activity and of course, its source and method of isolation. The actual analysis of product will vary depending on the member of the equine species which serves as the source, for example horse versus donkey. It may even vary when different individuals of the same type are used. For example, the amounts of glycine in the products isolated from several different burros may vary.

A series of tests were performed to more fully characterize the hemostatic fibrillar collagen composition of this invention. A homogenate of burro aortic tissue was incubated with α-chymotrypsin, dialyzed and the retentate pelleted by ultracentrifugation and resuspended in Tyrode's solution to form a stock solution. Aliquots of this stock solution were treated with Tyrode's solution containing purified collagenase. Other aliquots were treated with collagenase solution which had been boiled for fifteen minutes. After incubation with α-chymotrypsin, the platelet aggregating ability was retained. Incubation of the stock solution with collagenase produced rapid and complete destruction of the aggregator activity characterized by a prolongation of time to the onset of platelet aggregation, a conspicuous decrease in the velocity of aggregation, and a marked deterioration in the aggregator potency. The collagenase that had been boiled prior to incubation with the stock solution had no deleterious effects on platelet aggregating activity or potency.

Histochemical staining was performed by first precipitating fibrillar collagen from a burro aorta extract (dialyzed). To 7.5 ml (15 mg dry solids) of the dialyzed extract was added an equal volume of Millonig's buffered 0.1 glutaraldehyde solution, pH 7.4. After overnight incubation, the precipitated fibrils were pelleted by centrifugation (650×g for 30 minutes). The precipitate was washed with distilled water and directly stained with Verhoeff's elastica stain and Von Gieson's collagen counterstain. The stained fibrillar material was dehydrated and cleared and mounted on a glass slide for microscopic examination. Another aliquot of the dialyzed extract was precipitated and preserved with 10 ml of Millonig's phosphate buffered 0.1% glutaraldehyde. The microfibrillar material was washed and stained with aqueous 1% phosphotungstic acid (pH 2.3). In high magnification scanning electron microscopy, the burro fibrillar aortic collagen of this invention appears ultra thin (about 500 Å diameter) fibers with multiple well stained subbands between the major bands. This ultrastructural banding is similar to that reported for other fibrillar collagen. Amino acid analysis has indicated that fibrillar collagen of this invention resembles typ I collagen species reported in rat skin and tendon and human aortas. These collagen species are described in the following references: Gallop et al, "Posttranslational protein modifications, with special attention to collagen and elastin", *Physical Rev.*, 55:418–487, 1975; Barnes et al, "Platelet aggregating activity of type I and type III collagens from human aorta and chicken skin", *Biochem J.*, 160:647–651, 1976; McCullagh et al, "Collagen characterization and cell transformation in human arteriosclerosis", *Nature*, 268:73–75, 1975; Trelstad, "Human aorta collagens: Evidence for three distinct species", *Biochem Biophys. Res Comm*, 57:717–725, 1974.

While it is not understood just how the fibrillar collagen of this invention functions in its natural environment, it is believed that the collagen functions differently in its extracted form. The platelet aggregating action of the extracted collagen, even for autologous platelets, is accelerated over natural equine blood clotting. Internal injection in a guinea pig of a very dilute solution of extracted equine arterial fibrillar collagen (the highest dilution still domonstrating platelet aggregating proerties) produced a dramatic rise in blood pressure, accompanied by extensive thrombus formation and acute heart attack. The rapid rise in blood pressure illustrates the vasoconstrictor action of the extracted fibrillar arterial collagen, which enhances its utility for controlling bleeding.

The extracted arterial fibrillar collagen composition of this invention is the fibrillar collagen separated from its native arterial structural surroundings, regardless of the particular separation method or extractant used. In nature, the fibrillar collagen is not known to exist separate from surrounding arterial tissue. Nevertheless, this invention in its composition and method of use aspects is not intended to include arterial fibrillar collagen which becomes separated from its natural structural surroundings without human assistance.

The hemostatic agent of this invention comprises a suspension of platelet aggregating material in a carrier. Tyrode's solution is preferred as the carrier because it has been shown to contain nothing which deactivates the platelet aggregating function of the collagen. It will be apparent to workers in the art that many other aqueous solutions would be suitable carriers, for example, conventional saline solutions, balanced salt solutions such as Hank's solution, or Earle's solution. The preferred carrier for frozen storage is pure water, however, it is preferred for clinical testing purposes that the fibrillar collagen be resuspended in a balanced salt solution. For use to control bleeding, the carrier can be any externally administrable pharmaceutical carrier in which the fibrillar collagen can be dispersed sufficiently for use. The preferred carrier is an aqueous salt free solution that is provided as described above by dialysis against water. Antibiotics, such as penicillin and streptomycin, can be added to the salt free solution if desired for use in treating wounds, incisions, etc. It has been found that the hemostatic material of this invention is highly stable in the presence of antibiotics and when frozen at $-85°$ C. for long term storage.

One use of the extracted equine arterial hemostatic compositions is as a diagnostic tool to provide information about platelet function in human and other warm blooded species, e.g. mammals. It appears that platelets are more sensitive to this material than to any known commercial product or arterial collagen of other species. By contacting a solution containing platelets (e.g. plasma, or whole blood) with a composition of this invention and comparing the aggregation response to that of normal patients, platelet dysfunctions or hemostatic disorders can be detected. Platelet dysfunction is characteristic of several diseases. Some drugs such as aspirin have shown to affect platelet activity. Minor differences in platelet activity can be detected by the response to the composition of this invention, thus indicating the course of treatment, e.g. avoidance of the drug. The products of this invention are highly sensitive for detecting hyperactive platelets such as are associated with coronary heart disease, myocardial ischemia, and myocardial infarction. In addition, the extractable product of this invention is a valuable research tool for studying the role of platelet activity in such diseases as arteriosclerosis, heart attack, stroke, pulmonary embolism, drug toxicity, and ingestion of toxic metal pollutants such as cadmium.

Another utility for the hemostatic compositions of this invention is to stimulate the clotting of blood in wounds or surgical incisions, including skin grafts. The fibrillar collagen, like other animal collagen species, is expected to be compatible for internal applications, such as for controlling hemorrhaging from ruptured organs during veterinary surgery. For this use, the material should be in a pharmaceutically compatible carrier, e.g. Hank's, Earle's or Tyrode's solution. Alternatively, the isolated material can be separated from solution, i.e. by freeze drying and applied as a sponge or powder.

The various methods of preparation and use of extracted products of this invention are illustrated by the following examples. It will be apparent to those skilled in the art that substantial variations can be made in the illustrated methods without destroying or interferring with platelet aggregating functions of the material and such variations are contemplated as equivalents of the invention herein described.

To establish the platelet aggregating activity of the products of this invention as referred to in some of the following examples, it was necessary to prepare protein rich plasma (PRP) and protein poor plasma (PPP) from selected subjects. Human subjects, when selected, were not permitted to ingest aspirin or any other medication for ten days prior to testing. Whole blood was drawn from a juglar (animal) or forearm (human) vein through a disposable sterile silicone-treated needle, using a sterile plastic (35 ml) syringe previously wetted with a filter sterilized anticoagulant of 3.8% trisodium citrate dihydrate and 0.5% deterose in triple distilled water (pH 7.0). Collections of blood were immediately admixed with 0.1 volume of the anticoagulant in capped polystyrene tubes to avoid glass activation of platelets and plasma. Differential slow centrifugation at 22° C. was used to prepare citrated PRP. Equine blood was centrifuged once at 95 G for fifteen minutes; other animal or human blood was centrifuged twice (when necessary) sequentially at 95 G for thirty minutes and the two fractions cooled. The PRP was collected with a disposable polyethylene bulb pipet. To prevent pH change and optimize the platelet function during tests, the PRP was stored at 22° C. in capped plastic tubes. PPP was obtained by centrifugation of the remaining blood at 650 G for twenty minutes. Platelet counts in the PPP were determined by phase contrast microscopy using 1% ammonium oxalate.

Assays of platelet aggregation activity and potency were carried out in flat bottom silicone coated test tubes 8.75×50 mm size using a self-calibrating photoelectric apparatus (Platelet Aggregation Profiler, Model PAP-2 Bio/Data Corporation, Willow Grove, Pa.) with an integrator for turbidimetric curve recordings.

EXAMPLE I

The platelet aggregating property of a group of aged burros (Equus asinus) were studied using three platelet stimulation materials; thrombin, adenosine diphosphate (ADP) and an aqueous extract of burro aortic tissue. Some of the group of burros had been irradiated by exposure to a nuclear device, some had been irradiated by exposute to $^{182}Ta\gamma$ and others were unirradiated controls. Platelet dysfunction has been postulated as a symptom of radiation sickness. Whole blood was collected from the animals by jugular venipuncture using plastic (35 ml) syringes previously wetted with a filter sterilized citrate anticoagulant composed of 3.8% trisodium cirtrate (0.013 M) and 0.5% dextrose in glass distilled water (pH 7.0). Platelet rich plasma (PRP), 45 ml, was obtained from 60 ml whole blood centrifuged at 150×g for ten minutes at 22° C. Platelet poor plasma (PPP) was obtained by centrifugation of the remaining blood at 650×g for twenty minutes. Platelet aggregation stimulators were prepared as follows: stock ADP, grade I sodium salt from equine muscle (obtained from Sigma Chemical Company, St. Louis, Mo.) was dissolved in barbital buffer (pH 7.0) to produce a concentration of $2 \times 10^{-4}$ M. Aliquots of 0.5 ml were frozen ($-20°$ C.) and stored in capped plastic tubes. The contents of a tube was thawed and 0.05 ml of stock ADP was added to 0.45 ml of burro citrated PRP to produce a final concentration of 20 micro moles of ADP. Stock thrombin, (grade II thrombin 1000 NIH units/ml in 0.05 M phosphate buffer at pH 7.0) from beef plasma (Sigma Chemical Company) was diluted in 0.15 M NaCl to produce a concentration of 25 units of thrombin/ml. The equine aortic extracts were prepared as follows: the aortic arch and upper thoracic aortas of each of two burros (one irradiated and one unirradiated) were excized and rinsed in 0.15 M NaCl solution to provide working material; the loose connective tissue was dissected from the exterior surface of the arterial wall. After more than five repetitive rinsings in large volumes of saline solution and dissection the remaining loose surface connective tissue was dissected away. The cleansed vessel walls, predominantly tunica media and tunica intima, were cut in 5 mm square pieces. The cut issues were exhaustively washed free of all visible loosely adhered blood elements with Tyrode's solution. Finally, the pieces of aorta were rinsed several times in twenty-five volumes of filter sterilized Tyrode's solution. The cut, washed and drained tissues were packed in plastic petri plates, frozen ($-20°$ C.) and stored. A day before extractable material was desired for testing, pieces of the frozen tissue were weighed, immersed in cold filter sterilized Tyorde's solution 1 g/20 ml) and blended in a macrohomogenizer (Vertis, Model 3, Scientific Products, Stone Mountain, Ga.). Moderate to high speed mincing (23,000 rpm) was performed for five minutes. Blending was in a Lucite cooling cup packed in wet ice to avoid heat denaturation. The suspension of blended tissue was held overnight at 4° C. and centrifuged at $650 \times g$ for ten minutes. The desired extractable platelet stimulator from the aorta was contained in the supernatant phase. The extract was packed in wet ice and held at 4° C. and showed no deterioration in the platelet aggregating ability after thirty-six hours.

The response of the platelets to ADP, thrombin and to the aortic extract solution was evaluated by means of a self-calibrating aggregometer (Platelet Aggregation Profiler, Bio/Data Corporation, Willo Grove, Pa.) with an integrated recorder. Such devices are typically used in clinical laboratories to study platelet action. The platelet aggregation response to ADP was calculated as the maximum percentage decrease in optical density (OD) of the PRP reaction mixture stirred at 37° C. for periods up to ten minutes. The maximal velocity of platelet aggregation (OD decrease in percent) was calculated from the slope of the tangent line to the downward inclination of the optical density tracing during themost rapid phase of platelet flocculation. The response to thrombin was measured as (1) the delay time in seconds to the formation and contraction of a reactive platelet means followed by plasma clotting, and (2) the rate of platelet aggregation response expressed as maximum slope/sec $\times$ 100. The platelet response to the extracted aortic material was measured as (1) the lag phase time in seconds to the induction of platelet aggregation, (2) the maximal % decrease in OD of the reaction and (3) the maximal velocity of the platelet flocculation (maximum slope/second $\times$ 100). To calibrate the aggregation profiler, a series of measurements were taken at various platelet concentrations. The log of the platelet count varied essentially linearly with the optical density.

The platelet aggregation results are shown in Tables I, II and III. For both the ADP additions and the aortic extract, between 200,000 and 240,000 platelets/microliter of platelet rich plasma produced optimal reaction. As shown, it appears that the extract from the irradiated burro was measurably more effective than the extract from the unirradiated burro. This effect was believed to be caused by a radiation induced late somatic effect. It has since been shown that some unirradiated burros also have large amounts of fibrillar arterial collagen. It can be seen from Tables I, II and III that the aortic extract was substantially superior to the ADP and the throbmin solutions, particularly with respect to the velocity of aggregation. In humans, the platelet response to ADP is generally lower than response to the collagen. The interaction of the aortic extract with the platelets was characterized by (1) a distinctive delay time to the induction of platelet flocculation, (2) a high velocity of platelet clumping and (3) irreversible platelet aggregation. The response are typical of collagen-platelet interactions.

The extracted platelet aggregating activity in suspension in Tyrode's solution was insensitive to heating in a water bath at 56° C. for sixty minutes. The platelet aggregating activity was abolished by immersing the extract into a boiling water bath for fifteen minutes. Upon freezing at $-20°$ C. and thawing, platelet extract retains all of its platelet aggregating potency. Sonication of the material subsequent to freeze preservation and thawing is not required to unmask the activity and might even be harmful. The platelet aggregating material was nondialyzable from the Tyrode's solution against three changes in forty volumes of Tyrode's solution for seven days at 4° C. with continuous magnetic stirring. The protein concentration of extractable aortic material in two preparations from the aorta from unirradiated burro was 2030 and 2080 micrograms of protein/ml against bovine serum albumin as standard. Four preparations of extract from the aorta from the irradiated burro had concentrations of 1900, 1200, 2100 and 1380 micrograms of protein/ml. Ultracentrifugation of the aqueous supernatant at $105,000 \times g$ for one hour at 4° C. produced a soluble phase and a pellet of gelatinous material. The soluble phase had 75% of the original protein. The platelet aggregating agent was entirely contained in the gelatinous pellet. The irradiated burro from which aortic extract was obtained was about twenty-six years old and had been exposed to 545 R of $^{182}$Ta total body $\gamma$-radiation at 27.7 R/hr. about twenty-four years prior to death. The unirradiated burro was about twenty-one years old at death.

TABLE I

| Burro Platelet-Aggregation Responsiveness to Strong ADP | | | | | |
|---|---|---|---|---|---|
| ADP | Average OD decrease (in %) after | | | | Average Maximal velocity of aggregation (ADP slope/ second) $\times$ 100 |
| (in μmole/ 0.45 ml of PRP) | 1 minute | 3 minutes | 9 minutes | Maximum | |
| Unirradiated controls (3 burros) | | | | | |
| 40 (n = 8) | 29 | 47 | 41 | 48 | 59 |

TABLE I-continued

Burro Platelet-Aggregation Responsiveness to Strong ADP

| ADP (in μmole/ 0.45 ml of PRP) | Average OD decrease (in %) after | | | | Average Maximal velocity of aggregation (ADP slope/ second) × 100 |
|---|---|---|---|---|---|
| | 1 minute | 3 minutes | 9 minutes | Maximum | |
| 20 (n = 8) | 33 | 52 | 48 | 55 | 64 |
| Irradiated Burros ($^{182}$Ta γ-radiation) (3 burros) | | | | | |
| 40 (n = 7) | 26 | 46 | 44 | 51 | 50 |
| 20 (n = 7) | 27 | 47 | 49 | 55 | 58 |
| Irradiated Burros (nuclear device) (4 burros) | | | | | |
| 40 (n = 10) | 29 | 52 | 50 | 56 | 59 |
| 20 (n = 11) | 29 | 51 | 47 | 54 | 62 | n = No. of repetitive tests

TABLE II

Burro Platelet Reactions to Strong and Weak Thrombin

| Thrombin (in units/ 0.90 ml of PRP) | Average Delay time to PRP-plasma clotting (in seconds) | Average Maximal velocity of aggregation ((thrombin slope/ second) × 100 |
|---|---|---|
| Unirradiated Controls (3 burros) | | |
| 0.50 (n = 12) | 75 | 92 |
| 0.25 (n = 9) | >300 | 17 |
| Irradiated Burros ($^{182}$Ta γ-radiation) (3 burros) | | |
| 0.50 (n = 8) | 60 | 73 |
| 0.25 (n = 7) | >300 | 23 |
| Irradiated Burros (nuclear device) (4 burros) | | |
| 0.50 (n = 15) | 69 | 76 |
| 0.25 (n = 14) | 199 | 57 | n = No. of repetitive tests

TABLE III

Unirradiated Burro PRP Reaction to Extracts from Aortas of Unirradiated and Irradiated Burros

| Aorta collagen stimulator(s) (dose in ml/ 0.45 ml of PRP | Platelet reaction | | |
|---|---|---|---|
| | Lag phase (in seconds) | OD decrease maximum (in %) | Maximal velocity of aggregation (collagen ((slope/second) × 100) |
| Burro A86 (unirradiated) (control) | | | |
| 0.05 (n = 3) | 29 | 87 | 165 |
| 0.10 (n = 2) | 29 | 89 | 170 |
| Burro R52 (irradiated) | | | |
| 0.05 (n = 3) | 17 | 88 | 211 |
| 0.10 (n = 2) | 17 | 89 | 227 | n = No. of repetitive tests

EXAMPLE II

This example illustrates the platelet response of various animals, including humans, to arterial extracts from different irradiated and unirradiated burros. The aortic arch with the upper thoracic aorta of each of these burros was dissected and rinsed in three or more changes of 1 L volumes of 0.15 M NaCl solution. All visible loosely organized connective tissue was dissected from the outer surface of the arterial walls. Square cut pieces (about 5 mm) of aorta were rinsed in saline solution and exhaustively washed in Tyrode's solution to remove all loosely adsorbed plasma proteins and ahered blood elements. The cleansed tissue was drained, packed in plastic petri plates and frozen at −20° C. The aortic tissue (4 grms wt.) was blended in 80 ml of cold filter sterilized Tyrode's solution in the macrohomogenizer at 23,000 rpm for five minutes in a Lucite cooling cup packed in wet ice. The homogenate was stored overnight in 4° C. and then centrifuged at 650×g for ten minutes. The supernatant was separated and stored at 4° C. The remaining unextracted pelleted tissue was suspended in 40 ml of Tyrode's solution, again homogenized as above and stored overnight at 4° C. The second homogenate was centrifuged and the supernatant was removed. The two supernatants were pooled and blended in the macrohomogenizer. The resulting suspension was placed in a telescoped cellophane bag. It was dialyzed against thirty to forty volumes of Tyrode's solution with continuous magnetic stirring for seven to ten days at 4° C. 90 to 100 ml of of the dialyzed burro aorta extracts were obtained. After dialysis, the crude extracts (retentate) were pelleted by ultracentrifugation (105,000×g for one hour at 4° C.). The pellets were suspended in ½ volume of fresh Tyrode's solution and again blended in a macrohomogenizer. The preparation was designated as a 2× concentrate. For some experiments, 2× concentrates were intermixed with 3.90 M ammonium sulphate solution to a saturation of 46.2% (1.80 M). The precipitate which formed after storing in wet ice overnight at 4° C. was collected by centrifugation (650×g for thirty minutes). The pellet was resuspended in Tyrode's solution to the starting volume and again blended and dialyzed as described previously. All dilutions of the extracts were made in Tyrode's solutions. The diluted suspension can be stored in wet ice for seventy-two hours without undergoing any deterioration in platelet aggregation activity quality or potency. Table IV demonstrates the response of human PRP compared to horse and burro PRP. The aggregating agent was the retentate prior to ultracentrifugation. Table V demonstrates the response of burro platelets and human platelets for the more highly purified extracts. As seen, the morehighly purified reagents are consistently better at higher dilution than are the extracts shown in Table IV. Platelet response of humans and burros to like concentrations of extract contained in salt-free solution obtained by dialysis of the Tyrode's solution extract against water, were virtually the same as to the extract of Table V. In general for clinical testing and for controlling bleeding, the agent of this invention should be at the highest dilution which will provide the desired results, e.g. quick onset, 80+% aggregation, etc.

TABLE IV

Aggregability Effects on Equine and Human platelets

| Concentration of extract (in 0.05 ml/0.45 ml of PRP) | PRP of a horse | PRP of 8 burros (avg. response) | Hu-1 | Hu-2 | Hu-3 |
|---|---|---|---|---|---|

Delay time from stimulator addition to onset

TABLE IV-continued

Aggregability Effects on Equine and Human platelets

| Concentration of extract (in 0.05 ml/0.45 ml of PRP) | PRP of a horse | PRP of 8 burros (avg. response) | Hu-1 | Hu-2 | Hu-3 |
|---|---|---|---|---|---|
| of platelet aggregation (in seconds) | | | | | |
| Undiluted | 29 | 28 | 12 | 12 | 12 |
| 1:5 dilution | 36 | 37 | 17 | 14 | 14 |
| 1:10 | 43 | 43 | 17 | 22 | 18 |
| 1:20 | 55 | 52 | 19 | 24 | 19 |
| 1:40 | 77 | 63 | 24 | 28 | 24 |
| 1:80 | — | 72 | 34 | 29 | 29 |
| 1:160 | — | — | 48 | 43 | 31 |
| 1:320 | — | — | — | — | 38 |
| Maximal optical density decrease of PRP (% aggregation) | | | | | |
| Undiluted | 83 | 95 | 96 | 89 | 82 |
| 1:5 | 87 | 92 | 98 | 96 | 93 |
| 1:10 | 83 | 93 | 87 | 96 | 89 |
| 1:20 | 86 | 86 | 94 | 96 | 92 |
| 1:40 | 70 | 59 | 90 | 89 | 88 |
| 1:80 | — | 27 | 68 | 85 | 85 |
| 1:160 | — | — | 18 | 11 | 84 |
| 1:320 | — | — | — | — | 42 |
| Maximal velocity of the platelet aggregation (collagen slope/second × 100) | | | | | |
| Undiluted | 139 | 166 | 220 | 209 | 154 |
| 1:5 | 135 | 141 | 219 | 199 | 172 |
| 1:10 | 119 | 122 | 198 | 208 | 154 |
| 1:20 | 97 | 84 | 198 | 208 | 154 |
| 1:40 | 60 | 56 | 155 | 174 | 146 |
| 1:80 | — | 32 | 89 | 116 | 116 |
| 1:160 | — | — | 30 | 25 | 83 |
| 1:320 | — | — | — | — | 32 |

TABLE V

Relative Affinity of Equine and Human Platelets for Purified Stimulator

| Concentration of aggregator in 0.05 ml/ 0.45 ml PRP (estimated μg dry weight) | Pelleted 2 × fraction (105,000 × g) PRP of 3 burros Avg. response | Reprecipitated (at 1.80 M saturation (NH4)2SO4) PRP of same burros Avg. response | PRP of Hu-2 |
|---|---|---|---|
| Delay time from aggregator addition to onset of platelet aggregation (in seconds) | | | |
| Undiluted (52) | 9 | 8 | 6 |
| 1:5 dilution (10.4) | 11 | 13 | 7 |
| 1:10 (5.2) | 17 | 22 | 7 |
| 1:20 (2.6) | 22 | 26 | 10 |
| 1:40 (1.3) | 30 | 32 | 12 |
| 1:80 (0.65) | 33 | 42 | 14 |
| 1:160 (0.325) | 42 | 52 | 16 |
| 1:320 (0.163) | 59 | 71 (two*) | 19 |
| 1:640 (0.082) | 59 (two*) | — | 24 |
| Maximal optical density decrease of PRP (% aggregation) | | | |
| Undiluted | 95 | 97 | 88 |
| 1:5 | 97 | 98 | 89 |
| 1:10 | 95 | 95 | 98 |
| 1:20 | 92 | 95 | 92 |
| 1:40 | 90 | 87 | 96 |
| 1:80 | 83 | 79 | 94 |
| 1:160 | 70 | 42 | 86 |
| 1:320 | 34 | 12 | 87 |
| 1:640 | 5 | — | 54, 85** |
| Maximum velocity of aggregation (collagen slope/second) × 100) | | | |
| Undiluted | 195 | 241 | 262 |
| 1:5 | 205 | 248 | 262 |
| 1:10 | 181 | 171 | 262 |
| 1:20 | 149 | 165 | 218 |
| 1:40 | 125 | 123 | 218 |
| 1:80 | 110 | 99 | 186 |
| 1:160 | 84 | 43 | 155 |
| 1:320 | 48 | 24 | 137 |
| 1:640 | 14 | — | 60, **25 |

*No. of PRP specimens of 3 responding to added stimulus.
**Values of secondary wave of platelet aggregation and primary aggregation velocity response to the lowest concentration of the aggregator addition, respectively.

Example III describes the use of aqueous extractable equine arterial collagen for the treatment of wounds and for controlling bleeding and promoting healing, particularly of skin grafts.

EXAMPLE III

Two patches of skin, about 5×5 cm were removed from opposite sides of the back of an adult sow, and each was grafted to the open wound on the opposite side. One graft was performed without medication. The other graft was performed by first bathing the open wound and the underside of the graft with about 1 ml of aqueous aortic extract containing equine arterial fibrillar collagen, about 2 mg dry weight/cc. Bleeding was minimal for the graft using the aortic extract. Leakage of fluids accompanied the untreated graft. Healing of the treated graft appeared to be accelerated compared to the untreated graft.

EXAMPLE IV

The Example compares the platelet aggregating potency of a composition of this invention with collagen obtained from other species of mammals.

The procedure employed for studying the collagen/platelet interaction was the in vitro turbidimetric (optical density) technique as described in Born GVR:Nature, 194:927–929, (1962). In this example, platelet rich plasma (PRP) from anticoagulant treated, i.e. heparizined (Hep) or citrated (Citr) whole blood from a healthy burro was prepared by low speed centrifugation (150×g for ten minutes at 22° C.). Changes in light transmission through samples of Hep PRP and Citr PRP were continuously recorded on a strip-chart recorder by a Platelet Aggregation Profiler (Bio/Data Corporation, Willow Grove, Pa.). On the basis of comparable dilutions, quantative measurements were made of the aqueous extractable microfibrillar collagenous agents from the aortas of a burro, a pig, and a calf. The three microfibrillar collagenous agents were prepared in the same manner by blending aortic tissue in a macrohomogenizer in Tyrode's solution and dialyzing the homogenate against Tyrode's solution. The retentate, which contained the fibrillar collagen, was ultracentrifuged and the pellet resuspended in Tyrode's solution. The suspension was rehomogenized and dialyzed against triple distilled water (burro and calf) or Tyrode's solution (pig). Successive dilutions of the retentates in Tyrode's solution were made and 0.05 ml aliquots of the dilutions were contacted with 0.45 ml of the PRP and the optical transmission continuously recorded.

Table V displays the results of the three parameters measured.

1. The delay time (sec) to the initiation of platelet aggregation.
2. The intensity of platelet aggregation (% aggregation corresponds to % light transmitted).
3. The velocity of platelet clumping as indicated by the steepest slope of the optical transmission trace on the chart paper.

TABLE V

| Amount Of Aggr. Agents Contained In 0.05 ml Added To 0.45 ml Of Burro PRP | Delay Time To Onset Of Aggr. (In Secs) | | | | | Maximal Decrease In Optical Density Of PRP (% Aggregation) | | | | | Maximal Velocity Of Aggregation [(Max Slope/Sec) × 100] | | | | |
|---|---|---|---|---|---|---|---|---|---|---|---|---|---|---|---|
| Aortic Conc. | Burro | | Pig | Calf | | Burro | | Pig | Calf | | Burro | | Pig | Calf | |
| Burro PRP | Hep | Citr | Hep | Hep | Citr | Hep | Citr | Hep | Hep | Citr | Hep | Citr | Hep | Hep | Citr |
| Undiluted | 22 | 36 | 46 | 26 | 36 | 94 | 100 | 94 | 88 | 88 | 232 | 149 | 141 | 126 | 102 |
| 1:2 dilution | 23 | 41 | 48 | 34 | 43 | 98 | 100 | 92 | 94 | 70 | 189 | 141 | 104 | 124 | 77 |
| 1:5 dilution | 23 | 43 | 67 | 43 | 43 | 98 | 100 | 80 | 83 | 208 | 181 | 85 | 104 | 95 | |
| 1:10 dilution | 24 | 53 | 96 | 48 | 48 | 96 | 100 | tr | 70 | 72 | 189 | 154 | tr | 95 | 99 |
| 1:20 dilution | 29 | 67 | 0 | 50 | 65 | 94 | 100 | | 46 | 30 | 174 | 144 | | 61 | 58 |
| 1:40 dilution | 41 | 89 | | 60 | 108 | 90 | 100 | | 12 | tr | 139 | 141 | | 35 | tr |
| 1:80 dilution | 34 | 96 | | 0 | 0 | 94 | 100 | | | | 144 | 134 | | | |
| 1:160 dilution | 54 | 125 | | | | 96 | 100 | | | | 134 | 110 | | | |
| 1:320 dilution | 43 | 221 | | | | 94 | 66 | | | | 149 | 62 | | | |
| 1:640 dilution | 72 | 0 | | | | 54 | 0 | | | | 71 | 0 | | | |
| 1:1280 dilution | 108 | 0 | | | | tr | 0 | | | | tr | 0 | | | |

From an analysis of the table, it is apparent that the extracted equine arterial fibrillar collagen material of this invention is approximately 100 times more reactive than extracted pig arterial fibrillar collagen and approximately thirty times more reactive than extracted calf arterial fibrillar collagen.

EXAMPLE V

Thoracic aortas were obtained from twenty-five to thirty year old burros (*Equus asinus*) that had died from natural causes.

Isolation of Collagenous Fibrils—In experiment 1, eight 10 g samples of stock aortic segments were each placed in 50 ml of Tyrode buffer pH 7.2 containing 100 U and 100 μg of buffered pencillin G potassium and streptomycin sulfate per milliliter, respectively. The tissue, placed in a cooling cup packed in wet ice, was blended with a macrohomogenizer at 23,000 rpm for five minutes. After overnight extraction (4° C.), the homogenate was centrifuged (650×g for ten minutes at 0° to 4° C.). The viscous supernatant and the centrifugation "cushion", or "buffy", layer (which contained the platelet proaggregatory property) were separated with a plastic 5 ml pipet. The supernatant was filtered through a double layer, 2×2 inch, 12-ply sterile gauze and temporarily stored (4° C.), and the remaining pelleted tissue was reblended with Tyrode buffer. The centrifuged supernatant and "cushion" layer were again separated and filtered as described. The extraction process was repeated eight times in five days. The combined supernatants from the 1st and 2nd extractions were designated fraction a; extract from 3, 4, and 5 and 6, 7 and 8 sequential homogenization and steps of the remaining pelleted tissue were pooled and designated fractions b and c. The extracts (200 to 250 ml) were placed in telescoped Visking tubes and exhaustively dialyzed against two changes of Tyrode buffer (5 L) containing the added antibiotics, with constant stirring on a magnetic plate (4° C., five days).

After five days of dialysis, retentates in the tubes were fractionated by ultracentrifugation (105,000×g for thirty minutes at 0° to 2° C.). The pelleted material (which contained the total aggregant activity for platelets) was resuspended in approximately one-fifth volume of Tyrode buffer. The tissue was reblended in the macrohomogenizer for eight minutes, described above and the finely blended tissue concentrates were again exhaustively dialyzed in the cold (4° C.) against Tyrode buffer for five days. Finally, the extracts were dialyzed against triple distilled water with daily changes (5 L) for five days. The dialyzed, essentially salt-free tissue retentates were collected and distributed in small aliquots (0.5 to 3.5 ml) in plastic tubes with caps, frozen and stored (−85° C.).

In experiment 2, the same extraction steps were applied to seven 20 g samples of stock vascular tissue, and ten sequential blending and extraction steps were carried out in five days. The total filtered viscous aqueous extract plus the centrifugation "cushion" layer (4 L) were placed in telescoped tubing and exhaustively dialyzed an described above. Dialyzed retentates were fractionated twice by ultracentrifugation, and the pelleted vascular tissue was reblended with the macrohomogenizer (eight minutes) in one-fifth volume of Tyrode buffer. After exhaustive dialysis against buffer and distilled water, the essentially salt-free retentates were pooled and aliquots placed in plastic tubes with caps, frozen and stored (−85° C.).

In experiment 3, a 20 g sample of aortic segments was extracted with 200, 100 and 100 ml of Tyrode buffer with antiboitics on three consecutive days. From the extracts, a single salt-free concentrate was obtained. This preparation, after having been stored (−85° C.) for more than three years and repeatedly assayed for platelet aggregation effectiveness, still retained this biological property, both qualitatively and quantitatively.

Physiochemical Characterization—Determination of dry weight of the salt-free aortic extracts, protein assays by the micro-Kjeldahl method (bovine serum albumin and crystalline ammonium sulfate served as protein standards), and amino acid composition determination by the JEOL-JLC-6AH analyzer and a one-column system were carried out.

Total reducing carbohydrates were determined by a ferricyanide procedure with glucose as a standard; Part et al: *Handbook of Micromethods For Biological Sciences,* VanNostrand-Rheinhold Co., New York, 1974, pp 49–50.

The results are shown in Table IV and VII.

TABLE IV

Analytic Data of Salt-Free Fibrous Collagen Containing Extracts From Burro Aortas

| Preparation | dry weight aorta | mg dry weight isolated | Assays Protein (in mg per 100 mg dry wt.) | Carbohydrate |
|---|---|---|---|---|
| Expt. 1 Fraction | 80 | | | |
| a | | 426 | 47* | 14.9 |
| b | | 402 | 56 | 18.2 |
| c | | 760 | 85 | 5.5 |
| Expt. 2 | 140 | 2440 | 96** | 1.6 |
| Expt. 3 | 20 | 247 | 84 | ND |

*Precipitated at 40% saturation with ammonium sulfate. Precipitate reblended with Tyrode buffer and dialyzed until salt-free.
**Twice fractionated by ultracentrifugation.

ND = Not determined.

TABLE VII

Amino Acids in Fibrous-Collagen-Containing Protein Extracts From Burro Aortas

| | Amino Acids As Residues Per 1000 Total Amino Acid Residues | | | | |
|---|---|---|---|---|---|
| | Expt. 1 | | | | |
| | a | b | c | Expt. 2 | Expt. 3 |
| Lysine | 45.9 | 38.1 | 29.8 | 38.8 | 49.2 |
| Histidine | 27.1 | 25.4 | 31.2 | 19.8 | 11.2 |
| Hydroxylysine | 3.4 | 7.4 | 4.8 | 10.7 | 5.5 |
| Arginine | 44.6 | 46.5 | 43.2 | 40.4 | 57.6 |
| Hydroxyproline | 9.7 | 24.6 | 20.1 | 14.5 | 40.6 |
| Aspartic Acid | 83.2 | 69.3 | 65.4 | 65.3 | 76.5 |
| Threonine | 46.3 | 39.4 | 38.1 | 38.0 | 34.8 |
| Serine | 45.1 | 49.7 | 40.3 | 37.3 | 35.5 |
| Glutamic Acid | 84.5 | 91.3 | 81.9 | 71.1 | 90.8 |
| Proline | 75.5 | 79.4 | 98.2 | 81.2 | 79.1 |
| Glycine | 139.3 | 200.6 | 206.5 | 182.0 | 178.2 |
| Alanine | 106.5 | 110.1 | 133.9 | 125.8 | 95.0 |
| ½ Cysteine | 39.4 | 16.3 | 13.2 | 35.2 | 5.8 |
| Valine | 66.1 | 58.4 | 57.6 | 67.9 | 56.2 |
| Methionine | 16.2 | 13.6 | 14.2 | 16.4 | 12.8 |
| Isoleucine | 40.0 | 31.7 | 26.7 | 38.5 | 35.3 |
| Leucine | 71.0 | 57.8 | 52.5 | 62.0 | 81.2 |
| Tyrosine | 21.7 | 12.7 | 15.3 | 24.1 | 19.3 |
| Phenylalanine | 34.6 | 27.6 | 27.1 | 30.9 | 35.2 |

EXAMPLE VI

To compare sensitivities of platelets from two normal human subjects toward the fibrous collagen on a dry weight basis, the activity of three of the vascular collagen preparations were measured by aggregometers, using ten comparable doses of the fibrous collagens, toward the human platelets. By analysis of variance of the multiple data collections (Table VII), differences in the platelet sensitivities for the two human subjects were found to be significant (P<0.01) for nine levels of the three collagen preparations. These differences were reflected in all three parameters of the platelet responses measured (i.e., lag time to onset of flocculation, platelet aggregation intensity and aggregation velocity). The data indicated that platelets from the older of the two subjects were substantially more reactive. The data also clearly establishes the utility of the compositions of this invention for humans.

TABLE VII

Fibrous Collagen Activity Toward Platelets from Two Healthy Human Subjects*

| | Platelet reactivity (mean ± SE) | | | | | |
|---|---|---|---|---|---|---|
| | Delay time to onset | | Intensity (%) | | Velocity (%/min) | |
| Collagen dose** | Hu (30)*** | Hu (48) | Hu (30) | Hu (48) | Hu (30) | Hu (48) |
| ng | | | | | | |
| 15.6 | | 31.2 ± 2.1 | 0 | 64 ± 14 | 0 | 66 ± 11 |
| 31.25 | 40.8 ± 2.8 | 25.6 ± 2.1 | 4 ± 3 | 84 ± 3 | 15 ± 4 | 97 ± 6 |
| 62.5 | 27.2 ± 2.9 | 20 ± 1.7 | 63 ± 4 | 89 ± 1 | 70 ± 3 | 106 ± 3 |
| 125 | 21.2 ± 0.8 | 16.8 ± 0 | 77 ± 2 | 89 ± 1 | 111 ± 4 | 110 ± 4 |
| 250 | 16.4 ± 0.4 | 15.2 ± 0.4 | 81 ± 1 | 90 ± 1 | 102 ± 6 | 114 ± 14 |
| 500 | 14.4 ± 1.2 | 10.8 ± 0 | 81 ± 1 | 90 ± 0 | 96 ± 5 | 123 ± 14 |
| μg | | | | | | |
| 1 | 11.2 ± 1.4 | 8.4 ± 0.7 | 76 ± 2 | 92 ± 1 | 113 ± 4 | 134 ± 9 |
| 2 | 9.2 ± 1.1 | 8.4 ± 0 | 81 ± 2 | 88 ± 1 | 102 ± 3 | 126 ± 5 |
| 5 | 7.6 ± 0.4 | 6.4 ± 1.1 | 77 ± 1 | 87 ± 1 | 90 ± 7 | 127 ± 10 |
| 10 | 7.2 ± 1.2 | 6 ± 0.7 | 75 ± 1 | 80 ± 8 | 93 ± 3 | 89 ± 10 |

*PRP concentrates were prepared from blood sample collections from the two donors on successive days.
**Three different preparations of burro aortic fibrous collagen preparations were evaluated (see Tables VI and VII, experiments 1c, 2, and 3). An appropriate amount of the fibrous collagens in fine suspension in 50 μl of Tyrode buffer when added to 450 μl of the PRP concentrate and constantly stirred in the aggregometer at 37 C. for 7 min produced the observed platelet reactivity.
***Number in parentheses indicates age of male subject.

What is claimed is:

1. A method of preparing a hemostatic composition comprising the steps of:
   (a) contacting cleaned, homogenized equine arterial tissue with a balanced salt solution to provide an aqueous extract containing extracted collagen material and unextracted arterial tissue, and
   (b) separating unextracted arterial tissue from said aqueous mixture to provide an extract containing an arterial collagen material, said extract being capable of stimulating the aggregation of platelets in plasma or whole blood and containing a proteinaceous hemostatic agent characterized by the ability to enhance platelet aggregating activities in mammalian blood, being stable for extended periods of time at temperatures as low as −85° C., stable at 56° C. for up to 60 minutes, and when exposed to α-chymotrypsin, losing its platelet aggregating activity when exposed to collagenase at 37° C. or when heated at 100° C. for 15 minutes; containing a product having the following average number of amino acid residues per 1000 total amino acid residue:

| Lysine | 29.8 | Glycine | 206.5 |
|---|---|---|---|
| Histidine | 31.2 | Alanine | 133.9 |
| Hydroxylysine | 4.8 | ½ Cysteine | 13.2 |
| Arginine | 43.2 | Valine | 57.6 |
| Hydroxyproline | 20.1 | Methionine | 14.2 |
| Aspartic Acid | 65.4 | Isoleucine | 26.7 |

-continued

| | | | |
|---|---|---|---|
| Threonine | 38.1 | Leucine | 52.5 |
| Serine | 40.3 | Tyrosine | 15.3 |
| Glutamic Acid | 81.9 | Phenylalanine | 27.1 |
| Proline | 98.2 | | |

2. The method of claim 1 wherein the arterial tissue is burro aortic tissue.

3. The method of claim 1 wherein the arterial tissue is horse aortic tissue.

4. The method of claim 1 wherein the balanced salt solution is Tyrode's solution.

5. The method of claim 2 wherein the balanced salt solution is Tyrode's solution.

6. The method of claim 3 wherein the balanced salt solution is Tyrode's solution.

7. The method of claim 1 including the further step of (c) dialyzing the extract against water or a balanced salt solution to provide a substantially salt free retentate, said retentate being capable of stimulating the aggregation of platelets in plasma or whole blood and containing a proteinaceous hemostatic agent characterized by the ability to enhance platelet aggregating activities in mammalian blood, being stable for extended periods of time at temperatures as low as −85° C., stable at 56° C. for up to 60 minutes, and when exposed to α-chymotrypsin, losing its platelet aggregating activity when exposed to collagenase at 37° C. or when heated at 100° C. for 15 minutes; containing a product having the following average number of amino acid residues per 1000 total amino acid residue:

| | | | |
|---|---|---|---|
| Lysine | 29.8 | Glycine | 206.5 |
| Histidine | 31.2 | Alanine | 133.9 |
| Hydroxylysine | 4.8 | ½ Cysteine | 13.2 |
| Arginine | 43.2 | Valine | 57.6 |
| Hydroxyproline | 20.1 | Methionine | 14.2 |
| Aspartic Acid | 65.4 | Isoleucine | 26.7 |
| Threonine | 38.1 | Leucine | 52.5 |
| Serine | 40.3 | Tyrosine | 15.3 |
| Glutamic Acid | 81.9 | Phenylalanine | 27.1 |
| Proline | 98.2 | | |

8. The method of claim 7 wherein the arterial tissue is burro aortic tissue.

9. The method of claim 7 wherein the arterial tissue is horse aortic tissue.

10. The method of claim 7 wherein Tyrode's solution is used in both Step (a) and (c).

11. The method of claim 7 including the further step of (d) ultracentrifuging said retentate to separate suspended material and resuspending said separated material in fresh balanced salt solution to provide a suspension, said suspension being capable of stimulating the aggregation of platelets in plasma or whole blood and containing a proteinaceous hemostatic agent characterized by the ability to enhance platelet aggregating activities in mammalian blood, being stable for extended periods of time at temperatures as low as −85° C., stable at 56° C. for up to 60 minutes, and when exposed to α-chymotrypsin, losing its platelet aggregating activity when exposed to collagenase at 37° C. or when heated at 100° C. for 15 minutes; containing a product having the following average number of amino acid residues per 1000 total amino acid residue:

| | | | |
|---|---|---|---|
| Lysine | 29.8 | Glycine | 206.5 |
| Histidine | 31.2 | Alanine | 133.9 |
| Hydroxylysine | 4.8 | ½ Cysteine | 13.2 |
| Arginine | 43.2 | Valine | 57.6 |
| Hydroxyproline | 20.1 | Methionine | 14.2 |
| Aspartic Acid | 65.4 | Isoleucine | 26.7 |
| Threonine | 38.1 | Leucine | 52.5 |
| Serine | 40.3 | Tyrosine | 15.3 |
| Glutamic Acid | 81.9 | Phenylalanine | 27.1 |
| Proline | 98.2 | | |

12. The method of claim 11 wherein the arterial tissue is burro aortic tissue.

13. The method of claim 11 wherein the arterial tissue is horse aortic tissue.

14. The method of claim 11 wherein Tyrode's solution is used in Steps (a), (c) and (d).

15. The method of claim 11 including the further step of (e) dialyzing the suspension against water or a balanced salt solution to provide a substantially salt free retentate said retentate being capable of stimulating the aggregation of platelets in plasma or whole blood and containing a proteinaceous hemostatic agent characterized by the ability to enhance platelet aggregating activities in mammalian blood, being stable for extended periods of time at temperatures as low as −85° C., stable at 56° C. for up to 60 minutes, and when exposed to α-chymotrypsin losing its platelet aggregating activity when exposed to collagenase, at 37° C. or when heated at 100° C. for 15 minutes; containing a product having the following average number of amino acid residues per 1000 total amino acid residue:

| | | | |
|---|---|---|---|
| Lysine | 29.8 | Glycine | 206.5 |
| Histidine | 31.2 | Alanine | 133.9 |
| Hydroxylysine | 4.8 | ½ Cysteine | 13.2 |
| Arginine | 43.2 | Valine | 57.6 |
| Hydroxyproline | 20.1 | Methionine | 14.2 |
| Aspartic Acid | 65.4 | Isoleucine | 26.7 |
| Threonine | 38.1 | Leucine | 52.5 |
| Serine | 40.3 | Tyrosine | 15.3 |
| Glutamic Acid | 81.9 | Phenylalanine | 27.1 |
| Proline | 98.2 | | |

16. The method of claim 15 wherein the arterial tissue is burro aortic tissue.

17. The method of claim 15 wherein the arterial tissue is horse aortic tissue.

18. The method of claim 15 wherein Tyrode's solution is used in Steps (a), (b), (c) and (d).

19. A hemostatic agent isolatable from equine arterial tissue by extraction with aqueous solutions which is an equine arterial fibrillar collagen capable of stimulating the aggregation of platelets in plasma or whole blood and containing a proteinaceous hemostatic agent characterized by the ability to enhance platelet aggregating activities in mammalian blood, being stable for extended periods of time at temperatures as low as −85° C., stable at 56° C. for up to 60 minutes, and when exposed to α-chymotrypsin, losing its platelet aggregating activity when exposed to collagenase at 37° C. or when heated at 100° C. for 15 minutes; containing a product having the following average number of amino acid residues per 1000 total amino acid residue:

| | | | |
|---|---|---|---|
| Lysine | 29.8 | Glycine | 206.5 |
| Histidine | 31.2 | Alanine | 133.9 |
| Hydroxylysine | 4.8 | ½ Cysteine | 13.2 |
| Arginine | 43.2 | Valine | 57.6 |

| -continued | | | |
|---|---|---|---|
| Hydroxyproline | 20.1 | Methionine | 14.2 |
| Aspartic Acid | 65.4 | Isoleucine | 26.7 |
| Threonine | 38.1 | Leucine | 52.5 |
| Serine | 40.3 | Tyrosine | 15.3 |
| Glutamic Acid | 81.9 | Phenylalanine | 27.1 |
| Proline | 98.2 | | |

20. A hemostatic agent of claim 19 in a pharmaceutically acceptable carrier.

21. A hemostatic agent of claim 19 in an externally administerable pharmaceutically acceptable carrier.

22. A hemostatic agent of claim 19 in a balanced salt solution.

23. A hemostatic agent of claim 19 in water.

24. A method of stimulating platelet aggregation in mammalian plasma or whole blood which comprises contacting said plasma or whole blood with an amount which is effective to stimulate platelet aggregation of a hemostatic agent isolatable from equine arterial tissue by extraction with aqueous solutions which is an equine arterial fibrillar collagen capable of stimulating the aggregation of platelets in plasma or whole blood and containing a proteinaceous hemostatic agent characterized by the ability to enhance platelet aggregating activities in mammalian blood, being stable for extended periods of time at temperatures as low as −85° C., stable at 56° C. for up to 60 minutes, and when exposed to α-chymotrypsin, losing its platelet aggregating activity when exposed to collagenase at 37° C. or when heated at 100° C. for 15 minutes; containing a product having the following average number of amino acid residues per 1000 total amino acid residue:

| Lysine | 29.8 | Glycine | 206.5 |
|---|---|---|---|
| Histidine | 31.2 | Alanine | 133.9 |
| Hydroxylysine | 4.8 | ½ Cysteine | 13.2 |
| Arginine | 43.2 | Valine | 57.6 |
| Hydroxyproline | 20.1 | Methionine | 14.2 |
| Aspartic Acid | 65.4 | Isoleucine | 26.7 |
| Threonine | 38.1 | Leucine | 52.5 |
| Serine | 40.3 | Tyrosine | 15.3 |
| Glutamic Acid | 81.9 | Phenylalanine | 27.1 |
| Proline | 98.2 | | |

25. A method as in claim 24 wherein the hemostatic agent is in a pharmaceutically acceptable carrier.

26. A method on controlling external bleeding from a wound or incision comprising contacting said wound or incision with an amount which is effective to control bleeding of a hemostatic agent which is capable of stimulating the aggregation of platelets in plasma or whole blood and containing a proteinaceous hemostatic agent isolatable from equine arterial tissue by extraction with aqueous solutions as an equine arterial fibrillar collagen having the ability to enhance platelet aggregating activities in mammalian blood, being stable for extended periods of time at temperatures as low as −85° C., stable at 56° C. for up to 60 minutes, and when exposed to α-chymotrypsin, losing its platelet aggregating activity when exposed to collagenase at 37° C. or when heated at 100° C. for 15 minutes; containing a product having the following average number of amino acid residues per 1000 total amino acid residue:

| Lysine | 29.8 | Glycine | 206.5 |
|---|---|---|---|
| Histidine | 31.2 | Alanine | 133.9 |
| Hydroxylysine | 4.8 | ½ Cysteine | 13.2 |
| Arginine | 43.2 | Valine | 57.6 |
| Hydroxyproline | 20.1 | Methionine | 14.2 |
| Aspartic Acid | 65.4 | Isoleucine | 26.7 |
| Threonine | 38.1 | Leucine | 52.5 |
| Serine | 40.3 | Tyrosine | 15.3 |
| Glutamic Acid | 81.9 | Phenylalanine | 27.1 |
| Proline | 98.2 | | |

27. A method of detecting abnormal platelet function comprising contacting platelets which are suspected of abnormal function in plasma or whole blood under test with a hemostatic agent which is capable of stimulating the aggregation of platelets in plasma or whole blood and containing a proteinaceous hemostatic agent isolatable from equine arterial tissue by extraction with aqueous solutions characterized as an equine arterial fibrillar collagen having the ability to enhance platelet aggregating activities in mammalian blood, being stable for extended periods of time at temperatures as low as −85° C., stable at 56° C. for up to 60 minutes, and when exposed to α-chymotrypsin, losing its platelet aggregating activity when exposed to collagenase at 37° C. or when heated at 100° C. for 15 minutes; containing a product having the following average number of amino acid residues per 1000 total amino acid residue:

| Lysine | 29.8 | Glycine | 206.5 |
|---|---|---|---|
| Histidine | 31.2 | Alanine | 133.9 |
| Hydroxylysine | 4.8 | ½ Cysteine | 13.2 |
| Arginine | 43.2 | Valine | 57.6 |
| Hydroxyproline | 20.1 | Methionine | 14.2 |
| Aspartic Acid | 65.4 | Isoleucine | 26.7 |
| Threonine | 38.1 | Leucine | 52.5 |
| Serine | 40.3 | Tyrosine | 15.3 |
| Glutamic Acid | 81.9 | Phenylalanine | 27.1 |
| Proline | 98.2 | | | and comparing the aggregation response to the plasma or whole blood under study to the response of normal platelets.

* * * * *